United States Patent
Berlinger et al.

(10) Patent No.: US 11,042,993 B2
(45) Date of Patent: Jun. 22, 2021

(54) SOFT TISSUE STEREO-TRACKING

(71) Applicant: Brainlab AG, Munich (DE)

(72) Inventors: Kajetan Berlinger, Munich (DE); Birte Domnik, Munich (DE)

(73) Assignee: BRAINLAB AG, Munich (DE)

( * ) Notice: Subject to any disclaimer, the term of this patent is extended or adjusted under 35 U.S.C. 154(b) by 0 days.

(21) Appl. No.: 16/070,107

(22) PCT Filed: Oct. 9, 2017

(86) PCT No.: PCT/EP2017/075658
§ 371 (c)(1),
(2) Date: Jul. 13, 2018

(87) PCT Pub. No.: WO2019/072361
PCT Pub. Date: Apr. 18, 2019

(65) Prior Publication Data
US 2020/0388041 A1 Dec. 10, 2020

(51) Int. Cl.
*G06T 7/73* (2017.01)
*A61N 5/10* (2006.01)
(Continued)

(52) U.S. Cl.
CPC ............. *G06T 7/285* (2017.01); *A61N 5/103* (2013.01); *G06T 7/0012* (2013.01); *G06T 7/74* (2017.01);
(Continued)

(58) Field of Classification Search
CPC ..... G06T 3/0068; G06T 7/0012; G06T 7/285; G06T 7/30; G06T 7/32; G06T 7/38;
(Continued)

(56) References Cited

FOREIGN PATENT DOCUMENTS

| WO | WO2015127970 A1 | 9/2015 |
| WO | WO2017000988 A1 | 1/2017 |
| WO | WO2017001441 A1 | 1/2017 |

OTHER PUBLICATIONS

International Search Report and Written Opinion issued in International Patent Application No. PCT/EP2017/075658 dated Jan. 10, 2018.
(Continued)

*Primary Examiner* — Andrew W Johns
(74) *Attorney, Agent, or Firm* — Middleton Reutlinger

(57) ABSTRACT

The disclosed method encompasses reconstruction of a three-dimensional position of a tracking structure (which may comprise a target of radiation treatment) as reconstructed tracking structure data from pairs of two-dimensional tracking images which are input as tracking image data. Each tracking image contained in a pair of tracking images is compared to a tracking representation of the tracking structure contained in a search template image generated from the same perspective onto the tracking structure as the associated tracking image and input as search template data. The tracking image having the highest at local degree of similarity to its associated search template image is selected as a starting point (the first tracking image) for computing a corresponding image position (a complement point) in the other tracking image (the second tracking image) on the basis of applying epipolar geometry outgoing from the position in the first tracking image associated with the highest local degree of similarity. The method then continues with determining whether there is a point in the second tracking image having a higher degree of similarity than the complement point. Depending on the result of this analysis, an accumulated value of similarity is determined for each pair of tracking images depending on the sum of similarity values of the maximum similarity points in the first and second tracking images so determined. The position
(Continued)

of the tracking structure is determined as the intersection of back-projection lines of the points being associated with the highest sum of associated similarity values. Thereby, the reliability of position determination from stereoscopic two-dimensional x-ray images can be enhanced.

12 Claims, 2 Drawing Sheets

(51) Int. Cl.
*G06T 7/285* (2017.01)
*G06T 7/00* (2017.01)
*G06T 11/00* (2006.01)

(52) U.S. Cl.
CPC .. *G06T 11/006* (2013.01); *G06T 2207/10088* (2013.01); *G06T 2207/10124* (2013.01); *G06T 2207/30096* (2013.01)

(58) Field of Classification Search
CPC .. G06T 7/55; G06T 7/593; G06T 7/70; G06T 7/97; G06K 9/6201; G06K 9/6202; G06K 9/6215
See application file for complete search history.

(56) References Cited

OTHER PUBLICATIONS

Tang, et al. "A 3D Feature-Based Tracker for Multiple Object Tracking" Proc. Natl. Sci. Counc. (ROCA), vol. 23, No. 1. 1999.

Gendrin, et al. "Monitoring tumor motion by real time 2D/3D registration during radiotherapy" Radiotherapy and Oncology. Feb. 2012.

Tsai "A Versatile Camera Calibration Technique for High-Accuracy 3D Machine Vision Metrology Using Off-the-Shelf TV Cameras and Lenses" IEEE Journal of Robotics and Automation, vol. RA3, No. 4. Aug. 1987.

Yaniv "A Fluroscopic X-ray Image Processing and Registration for Computer-Aided Orthopedic Surgery" Institute of Computer Science, The Hebrew University of Jerusalem. Oct. 1, 1998.

Tsai "An Efficient and Accurate Camera Calibration Technique for 3D Machine Vision" Proceedings of the IEEE Conference on Computer Vision and Pattern Recognition. 1986.

SOFT TISSUE STEREO-TRACKING

FIELD OF THE INVENTION

The present invention relates to a computer-implemented method for determining the position of an anatomical tracking structure in a pair of tracking images usable for controlling radiation treatment, a corresponding computer program, a non-transitory program storage medium storing such a program and a computer for executing the program, as well as a radiation treatment system comprising an electronic data storage device and the aforementioned computer.

TECHNICAL BACKGROUND

The present invention relates to tracking tumours that move due to respiration shall be tracked using stereoscopic X-ray imaging to enable a highly accurate targeting in radiotherapy. Thus, treatment margins can be reduced and thus healthy tissue is spared. This new approach shall maximize the advantages of stereo tracking, using an efficient way to find the maximum accumulated similarity between the two representations in the just acquired image pair and the two representations in the previously defined tracking templates.

One known approach is to find out which of the two stereoscopic images is the better (i.e. the more trustworthy one, defined to be the master image), and then use the maximum similarity peak of that image relative to a template image showing a template of the tumour to compute the corresponding epipolar line in the other image. The maximum peak on this epipolar line (reduced search space) is then used to reconstruct the target position in space.

Drawbacks of this approach are:

When the decision about the master goes wrong, there is no way to correct that anymore. The result can dramatically be influenced by that wrong decision.

Results can only be built with the maximum peak of the master image. The maximum accumulated similarity measure of both stereoscopic images can be missed. Imagine having a fake maximum peak in both images, there is no chance to find the real target position anymore.

The present invention has the object of reliable determination of a tracking structure, for example for planning radiation treatment.

The present invention can be used for radiotherapy or radiosurgery procedures e.g. in connection with a system for image-guided radiotherapy or radiosurgery such as VERO® or ExacTrac®, both products of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The disclosed method encompasses reconstruction of a three-dimensional position of a tracking structure (which may comprise a target of radiation treatment) as reconstructed tracking structure data from pairs of two-dimensional tracking images which are input as tracking image data. Each tracking image contained in a pair of tracking images is compared to a tracking representation of the tracking structure contained in a search template image generated from the same perspective onto the tracking structure as the associated tracking image and input as search template data. The tracking image having the highest at local degree of similarity to its associated search template image is selected as a starting point (the first tracking image) for computing a corresponding image position (a complement point) in the other tracking image (the second tracking image) on the basis of applying epipolar geometry outgoing from the position in the first tracking image associated with the highest local degree of similarity. The method then continues with determining whether there is a point in the second tracking image having a higher degree of similarity than the complement point. Depending on the result of this analysis, an accumulated value of similarity is determined for each pair of tracking images depending on the sum of similarity values of the maximum similarity points in the first and second tracking images so determined. The position of the tracking structure is determined as the intersection of back-projection lines of the points being associated with the highest sum of associated similarity values. Thereby, the reliability of position determination from stereoscopic two-dimensional x-ray images can be enhanced.

GENERAL DESCRIPTION OF THE INVENTION

In this section, a description of the general features of the present invention is given for example by referring to possible embodiments of the invention.

In general, the invention reaches the aforementioned object by providing, in a first aspect, a computer-implemented medical method (for example, medical data processing method) for determining the position of an anatomical tracking structure in a pair of tracking images usable for controlling radiation treatment such as at least one of radiotherapy or radiosurgery of a patient. The method comprises executing, on at least one processor of at least one computer (for example at least one computer being part of the navigation system), the following exemplary steps which are executed by the at least one processor.

In a (for example first) exemplary step, tracking image data is acquired which describes (for example, defines or represents) a pair of two-dimensional (e.g. stereoscopic) tracking images of an anatomical body part of the patient containing (at least) the tracking structure. The pair of two-dimensional tracking images comprises for example a first tracking image and a second tracking image. The tracking structure may for example be target structure comprising a target of the radiation treatment (specifically, comprising tumour tissue), but may alternatively or additionally be any other anatomical structure comprising bony tissue (e.g. a part of the rib cage) or soft tissue (e.g. at least part of the diaphragm or the heart). The tracking image data is or has been generated by applying a medical imaging modality to at least the anatomical body part. In one example, the tracking images are radiographies (i.e. each tracking image is one—for example, exactly one—radiography, i.e. one two-dimensional x-ray image).

In a (for example second) exemplary step, search template data is acquired which describes (for example, defines or represents) a pair of two-dimensional search template images of the tracking structure. The pair of search template images comprises for example a first search template image associated with the first tracking image and a second search template image associated with the second tracking image. Specifically, the first search template image is used to search the first tracking image for the representation of the tracking structure shown on the first search template image, and the second search template image is used to search the second tracking image for the representation of the tracking structure shown on the second search template image. Therefore, the present disclosure defines that the first search template image is associated with the first tracking image and that the second search template image is associated with the second tracking image. For example, the search template data has been generated by applying a medical imaging modality to at least the tracking structure. For example, it has been generated from three-dimensional, for example, tomographic, planning image data describing the tracking structure such as a computed x-ray tomography (CT) or a magnetic resonance tomography (MRT). For example, each search template image is at least a part of a digitally reconstructed radiograph (DRR). Specifically, each search template image is at least part of exactly one DRR. Each search template image is or has been generated from the perspective of a medical imaging device (e.g. a flat panel x-ray imaging device) onto the tracking structure. That medical imaging device is used to generate the tracking image (from the same perspective onto the tracking structure) with which the respective search template image is associated.

In a (for example third) exemplary step, image similarity data is determined based on (e.g. from) the tracking image data and the search template data For example, the image similarity data describes (for example, defines or represents) at least one value (e.g. at least one local value defined for example as a value defining a measure of similarity between only one image unit of the tracking image and the only one corresponding image unit of the associated search template image and—if applicable—a neighbourhood defined around the position of the image unit) of similarity between each tracking image of the pair of tracking images and at least part of its associated search template image (i.e. between the first tracking image and the first search image and between the second tracking image and the second search image). For example, the image similarity data is determined based on a degree of similarity of the representation of the tracking structure in each one of the tracking images to the representation of the tracking structure in the associated search template image. The degree of similarity can be obtained for example by applying an image-unit-wise (such as pixel-wise or voxel-wise, respectively) correlation algorithm (for example, cross-correlation algorithm) or a difference computation (e.g. a minimum squared differences approach) to a pair of images consisting of one of tracking image and its associated search template image, and to a pair of images consisting of the other tracking image and its associated search template image. The similarity determination (e.g. the correlation algorithm or difference computation) may take into account a neighbourhood of image units (such as pixels or voxels, respectively) around the individual image unit being analyzed. The correlation or difference computation results in a description of the similarity of the colour values of the respective pair of images. The correlation or difference may for example be computed by moving one image over the other and/or overlaying the two images onto each other and executing the respective similarity computation on pair of overlaid image units (e.g. pixels). The result of the similarity determination may take the form of a matrix having the same coordinate as the tracking images and as the value at each of those coordinates, the similarity value for the image unit having the respective coordinate.

In a (for example fourth) exemplary step, image similarity peak data is determined based on (e.g. from) the image similarity data. The image similarity data describes (for example, defines or represents) for example a position of a first point (i.e. a first image unit) in the first tracking image having, among the pair of tracking images (and for example among all values described by the image similarity data), the highest value of similarity (as it is described by the image similarity data).

In a (for example fifth) exemplary step, complement peak data is determined based on (e.g. from) the tracking image data and the image similarity peak data. The complement peak data describes (for example, defines or represents) for example a position of a first point (i.e. a first image unit) in the second tracking image corresponding to (for example, having the same coordinates—such as image coordinates—as) the position of the first point in the first tracking image. Hereinforth, the first point in the second tracking image is also called complement point. For example, the complement peak data is determined by determining a back-projection line of the first point in the first tracking image and a position of a point associated with the maximum value of similarity on an epipolar line in the second tracking image, the epipolar line being associated with the back-projection line of the first point in the first tracking image (i.e. back-projection onto the imaging area of the imaging device used to generate the first tracking image), e.g. computed from the back-projection line of the first point in the in the first tracking image and relative to the second tracking image (i.e. relative to the imaging area of the imaging device used to generate the second tracking image).

In a (for example sixth) exemplary step, accumulated similarity data is determined based on (e.g. from) the complement peak data and the image similarity peak data The accumulated similarity data describes (for example, defines or represents) a sum of the similarity value associated with the first point (e.g. the similarity value of the first point) in the first tracking image and the similarity value associated with the complement point (e.g. the similarity value of the complement point).

In a (for example seventh) exemplary step, it is determined, based on (e.g. from) the tracking image data and the complement peak point data, whether there is a second (or, e.g. in a second or higher iteration of the method according to the first aspect, further) point in the second tracking image having a higher degree of similarity to at least part of the second search template image than the complement point. If it is determined that there is a second point in the second tracking image having a higher degree of similarity to the at least part of the second search template image than the complement point, the method continues with a for example eighth exemplary step in which next peak data is determined which describes (for example, defines or represents) for example the position of the second point in the second tracking image. The for example eighth exemplary step also encompasses determining reverse complement peak data based on (e.g. from) the tracking image data and the next peak data. The reverse complement peak data describes (for example, defines or represents) for example the position of a second (or, e.g. in a second or higher iteration of the method according to the first aspect, further) point in the first tracking image corresponding to (e.g. having the same coordinates as) the position of the second point in the second tracking image. Hereinforth, the second point in the first tracking image is also called reverse complement point.

For example, the complement peak data is determined by determining a back-projection line of the first point in the first tracking image and a position of a point associated with the maximum value of similarity on an epipolar line in the second tracking image, the epipolar line being associated with the back-projection line of the first point in the first tracking image (i.e. by back-projection of the first point in the first tracking image onto the imaging area of the imaging device used to generate the first tracking image), e.g. computed from the back-projection line of the first point in the in the first tracking image and relative to the second tracking image (i.e. relative to the imaging area of the imaging device used to generate the second tracking image).

The for example eighth exemplary step also encompasses determining next accumulated similarity data based on (e.g. from) the next peak data and the reverse complement peak data. The next accumulated similarity data describes (for example, defines or represents) for example a sum of the similarity value associated with the reverse complement point and the similarity value associated with the second point in the second tracking image.

If it is determined that there is no second (or, e.g. in a second or higher iteration of the method according to the first aspect, further) point in the second tracking image having a higher degree of similarity to the at least part of the second search template image than the complement point, execution of the method may be (for example, is) stopped.

In a (for example ninth) exemplary step, it is determined whether the sum described by the next accumulated similarity data is larger than the sum described by the accumulated similarity data.

If it is determined that the sum described by the next accumulated similarity data is larger than the sum described by the accumulated similarity data, the method according to the first aspect continues with a for example tenth exemplary step in which reconstructed tracking structure data is determined based on (e.g. from) the reverse complement peak data and the image similarity peak data. The reconstructed tracking structure data describes (for example, defines or represents) for example a three-dimensional position of the tracking structure (for example, its coordinates in a coordinate system usable for controlling a radiation treatment system such as the one according to the below-described radiation treatment system according to the fifth aspect). In one example, the reconstructed tracking structure data (specifically, the three-dimensional position of the tracking structure) is determined by determining the position of an intersection of the back-projection line of the first point in the first tracking image and a back-projection line of the first point in the second tracking image. The position of that intersection is then taken as the three-dimensional position of the tracking structure.

In one example (such as if it is determined that there is a second (or, e.g. in a second or higher iteration of the method according to the first aspect, further) point in the second tracking image having a higher degree of similarity to the at least part of the second search template image than the complement point), the reverse complement peak data is determined by determining a back-projection line of the second (or, e.g. in a second or higher iteration of the method according to the first aspect, further) point in the second tracking image (i.e. by back-projection of the second or, e.g. in a second or higher iteration of the method according to the first aspect, further point in the second tracking image onto the imaging area of the imaging device used to generate the second tracking image) and a position of a point associated with the maximum value of similarity on an epipolar line in the first tracking image, the epipolar line being associated with the back-projection line of the second (or, e.g. in a second or higher iteration of the method according to the first aspect, further) point in the second tracking image, e.g. computed from the back-projection line of the complement point and relative to the first tracking image (i.e. relative to the imaging area of the imaging device used to generate the first tracking image). For example, the reconstructed tracking structure data (specifically, the three-dimensional position of the tracking structure) is then determined by determining an intersection of the back-projection line of the second (or, e.g. in a second or higher iteration of the method according to the first aspect, further) point in the second tracking image and a back-projection line of the position of the point associated with the maximum value of similarity on the epipolar line in the first tracking image. The position of that intersection is then taken as the three-dimensional position of the tracking structure.

If, however, it is determined that the sum described by the next accumulated similarity data is not larger than the sum described by the accumulated similarity data, the reconstructed tracking structure data is determined in the for example tenth exemplary step based on (e.g. from) the complement peak data and the image similarity peak data.

If it is determined that the sum described by the next accumulated similarity data is not larger than the sum described by the accumulated similarity data, execution of the method may in on example be (for example, is) repeated starting with determining, based on the tracking image data and the complement peak point data, whether there is another second (or, e.g. in a second or higher iteration of the method according to the first aspect, further) point in the second image having a higher degree of similarity to the at least part of the second search template image than the complement point.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, for example the internet. The invention according to the second aspect therefore may alternatively or additionally relate to a data stream representative of the aforementioned program.

In a third aspect, the invention is directed to a non-transitory computer-readable program storage medium on which the program according to the fourth aspect is stored.

In a fourth aspect, the invention is directed to at least one computer (for example, a computer), comprising at least one processor (for example, a processor) and at least one memory (for example, a memory), wherein the program according to the fourth aspect is running on the processor or is loaded into the memory, or wherein the at least one computer comprises the computer-readable program storage medium according to the fifth aspect.

In a fifth aspect, the invention is directed to a radiation treatment system, comprising:
a) the at least one computer according to the fourth aspect;
b) at least one electronic data storage device storing at least the search template data; and
c) a medical imaging device (for example, a stereoscopic imaging device such as a stereoscopic flat panel x-ray imaging device) for generating the pair of tracking images; and
d) a radiation treatment apparatus comprising a treatment beam source (such as at least part of a particle accelerator or a radioactive substance) and a patient support unit (such as a patient bed which may have a controllable position relative to the treatment beam source), wherein the at least one computer is operably coupled to the at least one electronic data storage device for acquiring, from the at least one data storage device, at least the search template data, and
to the medical imaging device for acquiring, from the medical imaging device, the tracking image data and
to the radiation treatment apparatus for issuing a control signal to the radiation treatment apparatus for controlling at least one of
the functionality of the treatment beam source or
the position of the patient support unit (for example, relative to the treatment beam source) on the basis of the position of the tracking structure described by the reconstructed tracking structure data.

For example, if the tracking structure comprises the target of radiation treatment, it may be desirable that the position of the tracking structure lie in the isocentre of the radiation treatment system (for example, because radiation treatment planning is generally focussed on having the target structure in the isocentre), the position of the patient support unit may be changed (for example, by appropriately controlling a moving unit such as an electric motor to move the patient support unit) such that the target structure lies in the isocentre if it is determined that there is an offset between the position of the tracking structure described by the reconstructed tracking structure data. Alternatively or additionally, the treatment beam source may be moved to effect this change of position. Further alternatively or additionally, the functionality of the treatment beam source may be controlled by determining corresponding control data, for example to appropriately control emission of a treatment beam onto the patient if it is determined that there is an offset between the position of the tracking structure described by the reconstructed tracking structure data.

For example, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to planning radiation treatment, determining (e.g. electronically computing) a position of a tracking structure or determining control data for controlling a radiation treatment system on the basis of that position. For this reason alone, no surgical or therapeutic activity and in particular no surgical or therapeutic step is necessitated or implied by carrying out the invention.

The present invention also relates to the use of the radiation treatment system according to the fifth aspect or any embodiment thereof for planning or controlling radiation treatment (e.g. at least one of radiotherapy or radiosurgery). The use comprises for example at least one of the steps of the method according to the first aspect or the computer program according to the second aspect.

Definitions

In this section, definitions for specific terminology used in this disclosure are offered which also form part of the present disclosure.

Computer-Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Imaging Geometry

The information on the imaging geometry preferably comprises information which allows the analysis image (x-ray image) to be calculated, given a known relative position between the imaging geometry analysis apparatus and the analysis object (anatomical body part) to be analysed by x-ray radiation, if the analysis object which is to be analysed is known, wherein "known" means that the spatial geometry (size and shape) of the analysis object is known. This means for example that three-dimensional, "spatially resolved" information concerning the interaction between the analysis object (anatomical body part) and the analysis radiation (x-ray radiation) is known, wherein "interaction" means for example that the analysis radiation is blocked or partially or completely allowed to pass by the analysis object. The location and in particular orientation of the imaging geometry is for example defined by the position of the x-ray device, for example by the position of the x-ray source and the x-ray detector and/or for example by the position of the multiplicity (manifold) of x-ray beams which pass through the analysis object and are detected by the x-ray detector. The imaging geometry for example describes the position (i.e. the location and in particular the orientation) and the shape (for example, a conical shape exhibiting a specific angle of inclination) of said multiplicity (manifold). The position can for example be represented by the position of an x-ray beam which passes through the centre of said multiplicity or by the position of a geometric object (such as a truncated cone) which represents the multiplicity (manifold) of x-ray beams. Information concerning the above-mentioned interaction is preferably known in three dimensions, for example from a three-dimensional CT, and describes the interaction in a spatially resolved way for points and/or regions of the analysis object, for example for all of the points and/or regions of the analysis object. Knowledge of the imaging geometry for example allows the location of a source of the radiation (for example, an x-ray source) to be calculated relative to an image plane (for example, the plane of an x-ray detector). With respect to the connection between three-dimensional analysis objects and two-dimensional analysis images as defined by the imaging geometry, reference is made for example to the following publications:

1. "An Efficient and Accurate Camera Calibration Technique for 3D Machine Vision", Roger Y. Tsai, Proceedings of the IEEE Conference on Computer Vision and Pattern Recognition. Miami Beach, Fla., 1986, pages 364-374
2. "A Versatile Camera Calibration Technique for High-Accuracy 3D Machine Vision Metrology Using Off-the-Shelf TV Cameras and Lenses", Roger Y. Tsai, IEEE Journal of Robotics and Automation, Volume RA-3, No. 4, August 1987, pages 323-344.
3. "Fluoroscopic X-ray Image Processing and Registration for Computer-Aided Orthopedic Surgery", Ziv Yaniv
4. EP 08 156 293.6
5. U.S. 61/054,187

Treatment Beam

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts" or "target". These body parts are for example parts of a patient's body, i.e. anatomical body parts. Ionising radiation is for example used for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Imaging Methods

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body.

The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Elastic Fusion, Rigid Fusion, Image Fusion/Morphing

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
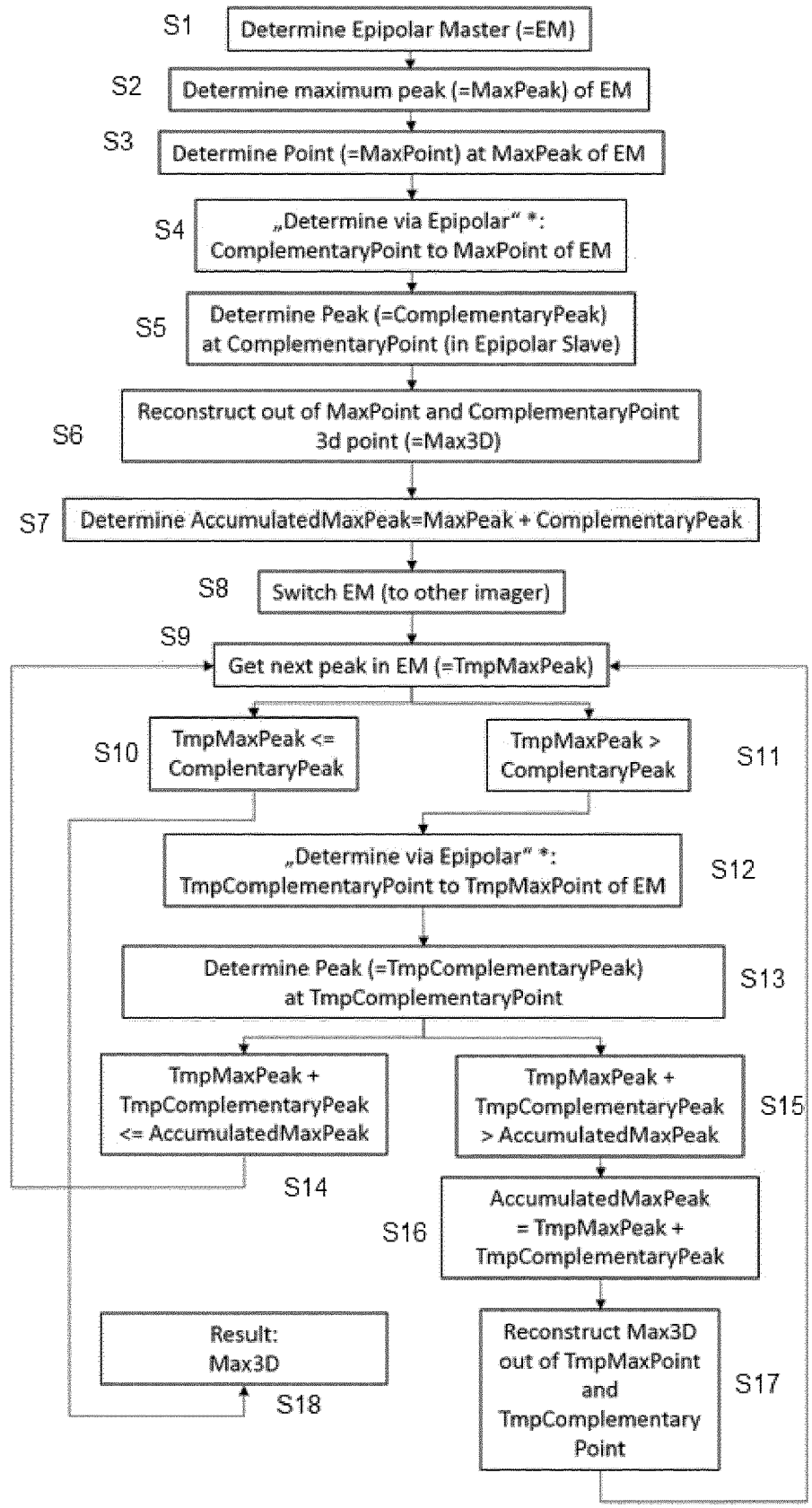
FIG. 1 illustrates a flow diagram of the method according to the first aspect.

FIG. 1 illustrates the basic steps of the method according to the first aspect. The illustration of FIG. 1 assumes that the tracking image data describing two two-dimensional images each showing a tracking representation of the tracking structure for one of two viewing directions has already been acquired from the medical imaging device 5 with a known spatial relationship between the viewing directions of the two-dimensional imaging units of the medical imaging device 5. Also, it is assumed that the search template data has already been acquired and that the image similarity data has already been determined. The image similarity data describes, for each of the two-dimensional images a similarity matrix to the corresponding tracking representation described by the search template images. Steps S1 to S3 encompass determining the image similarity peak data by classifying the two two-dimensional images into a primary and a secondary image (the master image and the slave image, respectively, corresponding to the first tracking image and the second tracking image, respectively). In step S1, the first tracking image is determined by determining, from the image similarity data, the tracking image having the maximum similarity value. The value (abbreviated MaxPeak) and the position of the maximum value (called MaxPoint) are determined in steps S2 and S3, respectively. Steps S4 and S5 encompass determination of the complement peak data by determining, applying the principles of epipolar geometry (step S4) to MaxPoint, the complementary point (abbreviated as ComplementaryPoint or and also called a complementary similarity benchmark). Determining ComplementaryPoint may include determining a primary alignment between the first tracking image and the corresponding tracking representation in the first search template image such that they match. The match may for example be implemented by overlaying the first tracking image and the first search template image and computing a correlation or difference (e.g. by applying a minimum squared differences approach) between the colour values of image units (e.g. pixels). From MaxPoint and ComplementaryPoint, the three-dimensional position of the tracking structure (abbreviated as Max3D) is reconstructed in step S6. In subsequent step S7, the accumulated similarity data is determined as the sum AccumulatedMaxPeak of the values of MaxPeak and ComplementaryPeak. This first accumulated similarity is stored as an accumulated similarity maximum and constitutes a first target result in space. Steps S8 to S15 are directed to subsequently computing for all similarities of the second tracking image that exceed the complementary similarity benchmark complementary alignments in the primary image using epipolar geometry, yielding second and third accumulated similarity values to be compared to the first accumulated similarity maximum;

second or third accumulated similarity values exceeding the first accumulated similarity maximum which shall replace the accumulated similarity maximum as a new accumulated similarity maximum; and a new result for the three-dimensional position of the tracking structure in case a new accumulated similarity maximum was determined.

In the following, a pseudocode representation of the method illustrated by FIG. 1 is discussed, in which "//" indicates the beginning of a comment which is not part of the pseudocode to be executed but serves the purpose of explaining the pseudocode written before "//". In detail, Peak1 (having the position PeakPoint1) being the maximum similarity value of the first tracking image and Peak2 (having the position PeakPoint2) being the maximum similarity value (i.e. degree of similarity) of the second tracking image are determined and serve as a basis for determining the tracking image received from the first imaging unit (Imager1) or the image received from the second imaging unit (Imager2) as the first tracking image (abbreviated as EpipolarMaster):

If (Peak1>Peak2)
EpipolarMaster=Imager1;
MaxPoint=PeakPoint1;
MaxPeak=Peak1;
Else
EpipolarMaster=Imager2;
MaxPoint=PeakPoint2;
MaxPeak=Peak2;

Then, the complementary point is computed in steps S4 and S5 by applying a procedure ComputeComplementaryPointViaEpipolar(.) (which represents an application of the principle of epipolar geometry) to MaxPoint relative to the position/the imaging area of the imager used for taking the tracking image not used as EpipolarMaster:

ComplementaryPoint=ComputeComplementaryPointViaEpipolar(MaxPoint);
ComplementaryPeak=PeakAt(ComplementaryPoint);

In the following step S7, AccumulatedMaxPeak is computed as:

AccumulatedMaxPeak=MaxPeak+ComplementaryPeak;

Max3D is computed in step S6 by applying a procedure Reconstruct3D(.) (which represents a procedure for computing the three-dimensional coordinates of the back-projection lines) to MaxPoint and ComplementaryPoint:

Max3D=Reconstruct3D(MaxPoint, ComplementaryPoint);

The analysis is then switched to the tracking image which was not selected as EpipolarMaster, by applying a corresponding procedure Switch(.) to EpipolarMaster (and the other tracking image corresponding to the second tracking image):

Switch(EpipolarMaster);

The other tracking image is then analysed as illustrated in steps S9 to S17:

While (True)
TmpMaxPoint=NextMax(EpipolarMaster); //TmpMaxPoint is the position of the maximum similarity value in the second tracking image-recall that EpipolarMaster is now the second tracking image
TmpMaxPeak=PeakAt(TmpMaxPoint); //TmpMaxPeak is the similarity value at the position TmpMax- Point and determined by applying a procedure PeakAt(.) for determining a value at a certain position (image position)

If (TmpMaxPeak<=ComplementaryPeak)//step S10 involving determining that there is no second point in the second tracking image having a higher degree of similarity to at least part of the second search template image than the complement point Break; //the program is stopped and Max3D is taken as the three-dimensional position of the tracking structure (step S18)

TmpComplementaryPoint=ComputeComplementaryPointViaEpipolar(TmpMaxPoint); //steps S11 and S12 involving determining that there is a second point in the second tracking image having a higher degree of similarity to at least part of the second search template image than the complement point TmpComplementaryPeak=PeakAt(TmpComplementaryPoint); //step S13 encompassing determination of the reverse complement peak data If (TmpMaxPeak+TmpComplementPeak>AccumulatedMaxPeak)//step S15

AccumulatedMaxPeak= TmpMaxPeak+TmpComplementaryPeak; //step S16

Max3D= Reconstruct3D(TmpMaxPoint, TmpComplementaryPoint); //step S17 involving determination of the reconstructed tracking structure data on the basis of the reverse complement peak data and the image similarity peak data—the method then returns to execution beginning from step S9

In step S14, the method returns to execution beginning from step S9 if it is determined that TmpMaxPeak+TmpComplementary Peak<=AccumulatedMaxPeak.

Figure 2:
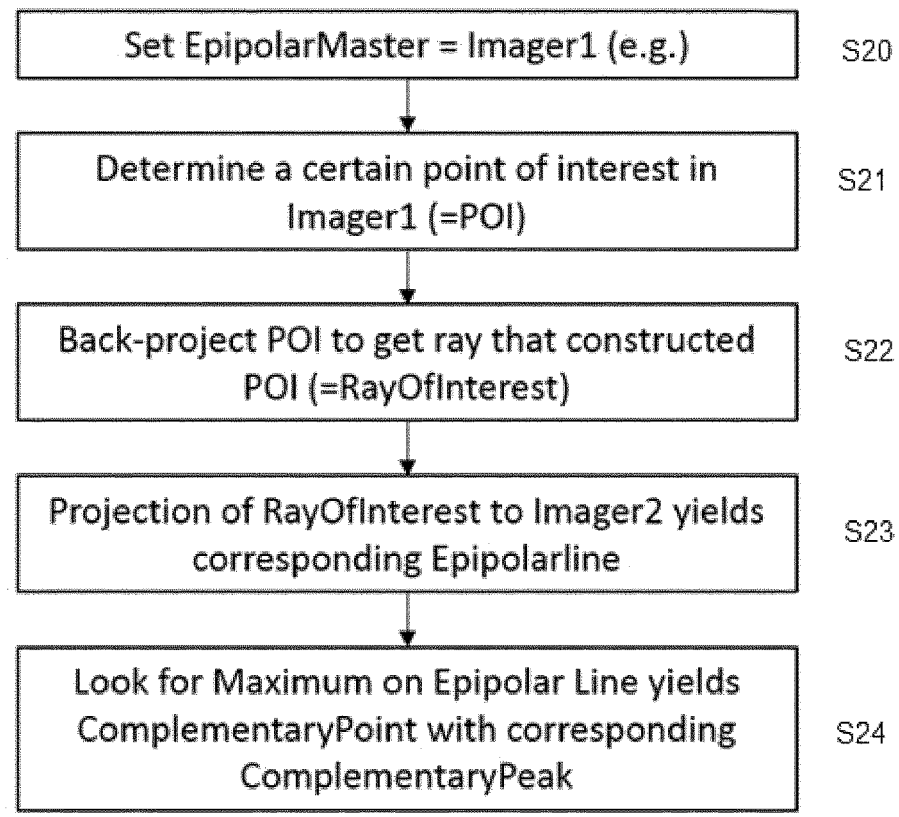
FIG. 2 shows an inset to the flow diagram of FIG. 1.

FIG. 2 describes an inset into the flow diagram of FIG. 1 for illustrating the steps of the procedure "Determine via Epipolar" (abbreviated above as ComputeComplementaryPointViaEpipolar(.)) which is mentioned in steps S4 and S12. In step S20, the tracking image Imager1 is set as EpipolarMaster (the first tracking image) and a point of interest is determined in Imager1 as step S21. That point is then back-projected to get a ray that constructed the point of interest in step S22. That ray is also called ray of interest. The projection of the ray of interest to the other (second) tracking image Imager2 yields the corresponding epipolar line in step S23. The ComplementaryPeak and its coordinates ComplementaryPoint are determined in step S24 by looking for the maximum along the epipolar line.

Figure 3:
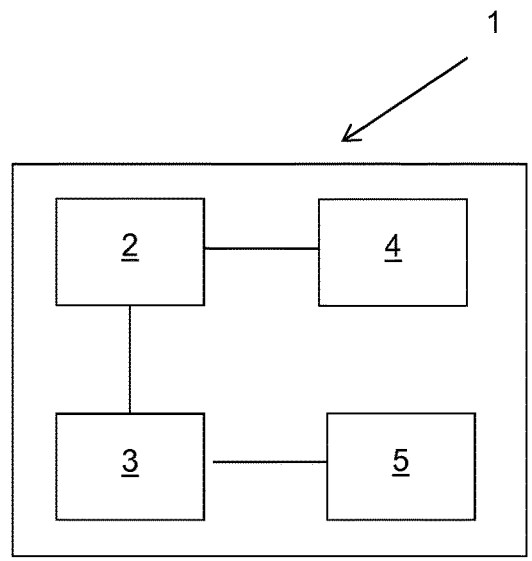
FIG. 3 is a schematic illustration of the system according to the fifth aspect.

FIG. 3 is a schematic illustration of the radiation treatment system 1 according to the fifth aspect. The system is in its entirety identified by reference sign 1 and comprises a computer 2, an electronic data storage device (such as a hard disc) 3 for storing at least the search template data and a radiation treatment apparatus 4 and a medical imaging device 5. The components of the radiation treatment system 1 have the functionalities and properties explained above with regard to the fifth aspect of this disclosure.

The method according to the first aspect maximizes the advantages of stereo tracking, because, contrary to the approach identified in the above section "Technical Background", the accumulated similarity is optimized. At first, the maximum peak of both images is determined (winner: master image, i.e. first tracking image; loser: slave image, i.e. second tracking image). Via epipolar geometry, the complementary peak in the respectively other image (the loser/second tracking image) is computed and stored. Thereby, a first possible three-dimensional detection is received, providing a first (temporary) accumulated similarity maximum. The idea is now to switch the epipolar master, and to compute for all similarity measure values of the "new" master image that exceed the stored complementary peak (and thus could potentially overtrump the stored (temporary) accumulated similarity maximum) via epipolar geometry potential new accumulated similarity maxima. Thereby, the above-described drawbacks of the known approach can be avoided.

The invention claimed is:

1. A computer-implemented method for determining a position of an anatomical tracking structure in a pair of tracking images usable for controlling radiation treatment of a patient, comprising:

acquiring tracking image data which describes a pair of two-dimensional tracking images of an anatomical body part of the patient containing the anatomical tracking structure, the pair of two-dimensional tracking images comprising a first tracking image and a second tracking image;

acquiring search template data which describes a pair of two-dimensional search template images of the anatomical tracking structure comprising a first search template image associated with the first tracking image and a second search template image associated with the second tracking image;

determining image similarity data based on the tracking image data and the search template data, wherein the image similarity data describes at least one at least local value of similarity between each tracking image of the pair of tracking images and at least part of its associated search template image;

determining image similarity peak data based on the image similarity data, which describes a position of a first point in the first tracking image having, among the pair of tracking images, the highest at least one at least local value of similarity;

determining complement peak data based on the tracking image data and the image similarity peak data, which describes a position of a first point in the second tracking image corresponding to the position of the first point in the first tracking image, the first point in the second tracking image being called complement point;

determining accumulated similarity data based on the complement peak data and the image similarity peak data, which describes a sum of the similarity value associated with the first point in the first tracking image and the similarity value associated with the complement point; determining, based on the tracking image data and the complement peak point data, whether there is a second point in the second tracking image having a higher degree of similarity to at least part of the second search template image than the complement point, wherein upon determining there is a second point in the second tracking image having a higher degree of similarity to the at least part of the second search template image than the complement point:

determining next peak data which describes the position of the second point in the second tracking image; and determining reverse complement peak data, based on the tracking image data and the next peak data, which describes the position of a second point in the first tracking image corresponding to the position of the second point in the second tracking image, the second point in the first tracking image being called reverse complement point; and determining next accumulated similarity data, based on the next peak data and the reverse complement peak data, which describes a sum of the similarity value associated with the reverse complement point and the similarity value associated with the second point in the second tracking image;

determining whether the sum described by the next accumulated similarity data is larger than the sum described by the accumulated similarity data, wherein upon determining the sum described by the next accumulated similarity data is larger than the sum described by the accumulated similarity data:

determining reconstructed tracking structure data based on the reverse complement peak data and the image similarity peak data, which describes a three-dimensional position of the anatomical tracking structure, and upon determining the sum described by the next accumulated similarity data is not larger than the sum described by the accumulated similarity data:

determining the reconstructed tracking structure data based on the complement peak data and the image similarity peak data.

2. The method according to claim 1, wherein the complement peak data is determined by determining a back-projection line of the first point in the first tracking image and a position of a point associated with the maximum value of similarity on an epipolar line in the second tracking image, the epipolar line being associated with the back-projection line of the first point in the first tracking image.

3. The method according to claim 2, wherein the reconstructed tracking structure data is determined by determining the position of an intersection of the back-projection line of the first point in the first tracking image and a back-projection line of the first point in the second tracking image.

4. The method according to claim 1, wherein, if it is determined that there is no second point in the second tracking image having a higher degree of similarity to the at least part of the second search template image than the complement point, execution of the method is stopped.

5. The method according to claim 1, wherein, if it is determined that the sum described by the next accumulated similarity data is not larger than the sum described by the accumulated similarity data, execution of the method is repeated starting with determining, based on the tracking image data and the complement peak point data, whether there is another second point in the second tracking image having a higher degree of similarity to the at least part of the second search template image than the complement point.

6. The method according to claim 1, wherein the reverse complement peak data is determined by determining a back-projection line of the second point in the second tracking image and a position of a point associated with the maximum value of similarity on an epipolar line in the first tracking image, the epipolar line being associated with the back-projection line of the second point in the second tracking image.

7. The method according to claim 6, wherein the reconstructed tracking structure data is determined by determining an intersection of the back-projection line of the second point in the second tracking image and a back-projection line of the position of the point associated with the maximum value of similarity on the epipolar line in the first tracking image.

8. The method according to claim 1, wherein the search template data has been generated from three-dimensional tomographic planning image data.

9. The method according to claim 1, wherein the tracking images are radiographies.

10. A non-transitory computer-readable program storage medium comprising computer instructions for determining a position of an anatomical tracking structure in a pair of images usable for controlling radiation treatment of a patient, executable by one or more processors to:

acquire tracking image data which describes a pair of two-dimensional tracking images of an anatomical body part of the patient containing the anatomical tracking structure, the pair of two-dimensional tracking images comprising a first tracking image and a second tracking image;

acquire search template data which describes a pair of two-dimensional search template images of the anatomical tracking structure comprising a first search template image associated with the first tracking image and a second search template image associated with the second tracking image;

determine image similarity data based on the tracking image data and the search template data, wherein the image similarity data describes at least one at least local value of similarity between each tracking image of the pair of tracking images and at least part of its associated search template image;

determine image similarity peak data based on the image similarity data, which describes a position of a first point in the first tracking image having, among the pair of tracking images, the highest at least one at least local value of similarity;

determine complement peak data based on the tracking image data and the image similarity peak data, which describes a position of a first point in the second tracking image corresponding to the position of the first point in the first tracking image, the first point in the second tracking image being called complement point;

determine accumulated similarity data based on the complement peak data and the image similarity peak data, which describes a sum of the similarity value associated with the first point in the first tracking image and the similarity value associated with the complement point;

determine, based on the tracking image data and the complement peak point data, whether there is a second point in the second tracking image having a higher degree of similarity to at least part of the second search template image than the complement point, wherein upon determining there is a second point in the second tracking image having a higher degree of similarity to the at least part of the second search template image than the complement point:

determine next peak data which describes the position of the second point in the second tracking image; and determine reverse complement peak data based on the tracking image data and the next peak data, which describes the position of a second point in the first tracking image corresponding to the position of the second point in the second tracking image, the second point in the first tracking image being called reverse complement point; and determine next accumulated similarity data based on the next peak data and the reverse complement peak data, which describes a sum of the similarity value associated with the reverse complement point and the similarity value associated with the second point in the second tracking image;

determine whether the sum described by the next accumulated similarity data is larger than the sum described by the accumulated similarity data, wherein upon determining the sum described by the next accumulated similarity data is larger than the sum described by the accumulated similarity data:

determine reconstructed anatomical tracking structure data based on the reverse complement peak data and the image similarity peak data, which describes a three-dimensional position of the anatomical tracking structure, and upon determining the sum described by the next accumulated similarity data is not larger than the sum described by the accumulated similarity data:

determine the reconstructed anatomical tracking structure data based on the complement peak data and the image similarity peak data.

11. An apparatus for determining a position of an anatomical tracking structure in a pair of images usable for controlling radiation treatment of a patient, comprising memory and one or more processors operable to execute instructions stored in the memory to:

acquire tracking image data which describes a pair of two-dimensional tracking images of an anatomical body part of the patient containing the anatomical tracking structure, the pair of two-dimensional tracking images comprising a first tracking image and a second tracking image;

acquire search template data which describes a pair of two-dimensional search template images of the anatomical tracking structure comprising a first search template image associated with the first tracking image and a second search template image associated with the second tracking image;

determine image similarity data based on the tracking image data and the search template data, wherein the image similarity data describes at least one at least local value of similarity between each tracking image of the pair of tracking images and at least part of its associated search template image;

determine image similarity peak data based on the image similarity data, which describes a position of a first point in the first tracking image having, among the pair of tracking images, the highest at least one at least local value of similarity;

determine complement peak data based on the tracking image data and the image similarity peak data, which describes a position of a first point in the second tracking image corresponding to the position of the first point in the first tracking image, the first point in the second tracking image being called complement point;

determine accumulated similarity data based on the complement peak data and the image similarity peak data, which describes a sum of the similarity value associated with the first point in the first tracking image and the similarity value associated with the complement point; determining, based on the tracking image data and the complement peak point data, whether there is a second point in the second tracking image having a higher degree of similarity to at least part of the second search template image than the complement point, wherein upon determining there is a second point in the second tracking image having a higher degree of similarity to the at least part of the second search template image than the complement point:

determine next peak data which describes the position of the second point in the second tracking image; and determine reverse complement peak data based on the tracking image data and the next peak data, which describes the position of a second point in the first tracking image corresponding to the position of the second point in the second tracking image, the second point in the first tracking image being called reverse complement point; and determine next accumulated similarity data based on the next peak data and the reverse complement peak data, which describes a sum of the similarity value associated with the reverse complement point and the similarity value associated with the second point in the second tracking image;

determine whether the sum described by the next accumulated similarity data is larger than the sum described by the accumulated similarity data, wherein upon determining the sum described by the next accumulated similarity data is larger than the sum described by the accumulated similarity data:

determine reconstructed anatomical tracking structure data based on the reverse complement peak data and the image similarity peak data, which describes a three-dimensional position of the anatomical tracking structure, and upon determining the sum described by the next accumulated similarity data is not larger than the sum described by the accumulated similarity data:

determine the reconstructed anatomical tracking structure data based on the complement peak data and the image similarity peak data.

12. A radiation treatment system for determining a position of an anatomical tracking structure in a pair of images usable for controlling radiation treatment of a patient, comprising:

at least one computer having at least one processor connected to memory, the memory having instructions stored thereon which when executed by the at least one processor causes the at least one processor to:

acquire tracking image data which describes a pair of two-dimensional tracking images of an anatomical body part of the patient containing the anatomical tracking structure, the pair of two-dimensional tracking images comprising a first tracking image and a second tracking image;

acquire search template data which describes a pair of two-dimensional search template images of the anatomical tracking structure comprising a first search template image associated with the first tracking image and a second search template image associated with the second tracking image;

determine image similarity data based on the tracking image data and the search template data, wherein the image similarity data describes at least one at least local value of similarity between each tracking image of the pair of tracking images and at least part of its associated search template image;

determine image similarity peak data based on the image similarity data, which describes a position of a first point in the first tracking image having, among the pair of tracking images, the highest at least one at least local value of similarity;

determine complement peak data based on the tracking image data and the image similarity peak data, which describes a position of a first point in the second tracking image corresponding to the position of the first point in the first tracking image, the first point in the second tracking image being called complement point;

determine accumulated similarity data based on the complement peak data and the image similarity peak data, which describes a sum of the similarity value associated with the first point in the first tracking image and the similarity value associated with the complement point; determining, based on the tracking image data and the complement peak point data, whether there is a second point in the second tracking image having a higher degree of similarity to at least part of the second search template image than the complement point, wherein upon determining there is a second point in the second tracking image having a higher degree of similarity to the at least part of the second search template image than the complement point:

determine next peak data which describes the position of the second point in the second tracking image; and determine reverse complement peak data based on the tracking image data and the next peak data, which describes the position of a second point in the first tracking image corresponding to the position of the second point in the second tracking image, the second point in the first tracking image being called reverse complement point; and determine next accumulated similarity data based on the next peak data and the reverse complement peak data, which describes a sum of the similarity value associated with the reverse complement point and the similarity value associated with the second point in the second tracking image;

determine whether the sum described by the next accumulated similarity data is larger than the sum described by the accumulated similarity data, wherein upon determining the sum described by the next accumulated similarity data is larger than the sum described by the accumulated similarity data:

determine reconstructed anatomical tracking structure data based on the reverse complement peak data and the image similarity peak data, which describes a three-dimensional position of the anatomical tracking structure, and upon determining the sum described by the next accumulated similarity data is not larger than the sum described by the accumulated similarity data:

determine the reconstructed anatomical tracking structure data based on the complement peak data and the image similarity peak data;

the at least one computer operable to control a radiation treatment apparatus having a treatment beam source combined with a patient support unit, wherein the at least one computer is operably coupled to the radiation treatment apparatus for issuing a control signal to the radiation treatment apparatus for controlling at least one of the functionality of the treatment beam source or the position of the patient support unit based upon the position of the anatomical tracking structure described by the reconstructed anatomical tracking structure data.

\* \* \* \* \*